(12) United States Patent
O'Rourke et al.

(10) Patent No.: US 10,512,633 B2
(45) Date of Patent: Dec. 24, 2019

(54) ALKALOIDS FROM SPONGE, SCAFFOLDS FOR THE INHIBITION OF HUMAN IMMUNODEFICIENCY VIRUS (HIV)

(71) Applicant: KING ABDULLAH UNIVERSITY OF SCIENCE AND TECHNOLOGY, Thuwal (SA)

(72) Inventors: Aubrie O'Rourke, Thuwal (SA); Stephan Kremb, Thuwal (SA); Christian R. Voolstra, Thuwal (SA)

(73) Assignee: KING ABDULLAH UNIVERSITY OF SCIENCE AND TECHNOLOGY, Thuwal (SA)

( * ) Notice: Subject to any disclaimer, the term of this patent is extended or adjusted under 35 U.S.C. 154(b) by 95 days.

(21) Appl. No.: 15/520,801

(22) PCT Filed: Oct. 23, 2015

(86) PCT No.: PCT/IB2015/002126
§ 371 (c)(1),
(2) Date: Apr. 20, 2017

(87) PCT Pub. No.: WO2016/067090
PCT Pub. Date: May 6, 2016

(65) Prior Publication Data
US 2018/0000787 A1 Jan. 4, 2018

Related U.S. Application Data

(60) Provisional application No. 62/068,716, filed on Oct. 26, 2014.

(51) Int. Cl.
| | | |
|---|---|---|
| A61K 31/4168 | (2006.01) | |
| A61K 31/4015 | (2006.01) | |
| C07D 207/327 | (2006.01) | |
| C07D 233/88 | (2006.01) | |
| G01N 33/50 | (2006.01) | |
| A61K 35/56 | (2015.01) | |
| G01N 30/02 | (2006.01) | |

(52) U.S. Cl.
CPC ...... *A61K 31/4168* (2013.01); *A61K 31/4015* (2013.01); *C07D 207/327* (2013.01); *C07D 233/88* (2013.01); *G01N 33/5008* (2013.01); *A61K 35/56* (2013.01); *C12N 2740/16063* (2013.01); *G01N 2030/027* (2013.01)

(58) Field of Classification Search
CPC ............ A61K 31/4168; A61K 31/4015; C07D 207/327; C07D 233/88
USPC .................................................. 514/212.01
See application file for complete search history.

(56) References Cited

U.S. PATENT DOCUMENTS

| | | |
|---|---|---|
| 5,834,609 A | 11/1998 | Horne et al. |
| 7,098,204 B2 | 8/2006 | Meijer |
| 7,838,681 B2 | 11/2010 | Al Mourabit et al. |
| 2003/0181375 A1 | 9/2003 | McSharry |
| 2007/0249655 A1 | 10/2007 | Kesteleyn et al. |
| 2010/0280004 A1 | 11/2010 | Anderson et al. |
| 2014/0142174 A1 | 5/2014 | Delaet et al. |

FOREIGN PATENT DOCUMENTS

WO   WO 01/041768   6/2001

OTHER PUBLICATIONS

International Search Report and Written Opinion received in connection with international application No. PCT/IB2015/002126; dated Feb. 24, 2016.
Al-Mourabit, A., et al. "Biosynthesis, asymmetric synthesis, and pharmacology, including cellular targets, of the pyrrole-2-aminoimidazole marine alkaloids". Nat Prod Rep 2011, 28, 1229-1260.
Alreefi, Hajar, Adel: "Determining the Effect of Red Sea Sponge: Associated Bacteria against HIV-1 integrase and HeLa Cancer Cell Line", 2014, (Abstract only) Retreived from: https://apps2.societyforscience.org/Abstracts/Search/ViewAbstract?projectid=13404.
Breton, J.J., et al, "The natural product hymenialdisine inhibits interleukin-8 production in U937 cells by inhibition of nuclear factor-kappa B", J Pharmacol Exp Ther 1997, 282, 459-466.
Bugni, T.S. et al., "Marine natural product libraries for high-throughput screening and rapid drug discovery". J Nat Prod 2008, 71, 1095-1098.
Butler, M.S., et al., "Natural product and natural product derived drugs in clinical trials". Natural Product Reports 2014, 31, 1612-1661.
Cimino, G. et al. "Isolation and x-ray crystal-structure of a novel bromo-compound from 2 marine sponges". Tetrahedron Lett 1982, 23, 767-768.
Clercq, D. "Curious discoveries in antiviral drug development: The role of serendipity". Medicinal Research Reviews 2015, 00, No. 0, 1-22, 2015.
Curman, D. et al., "Inhibition of the $G_2$ DNA damage checkpoint and of protein kinases Chk1 and Chk2 by the marine sponge alkaloid debromohymenialdisine.", J Biol Chem 2001, 276, 17914-17919.
Debebe, Z. et al., "Iron chelators of the di-2-pyridylketone thiosemicarbazone and 2-benzoylpyridine thiosemicarbazone series inhibit hiv-1 transcription: Identification of novel cellular targets—iron, cyclin-dependent kinase (CDK) 2, and CDK9", (vol. 79, p. 185, 2011). Mol Pharmacol 2011, 80, 1190-1190.
Downs, C.A. et al., "Oxidative stress and seasonal coral bleaching". Free Radical Biology & Medicine 2002, 33, 533-543.

(Continued)

Primary Examiner — Yevgeny Valenrod
(74) Attorney, Agent, or Firm — Pabst Patent Group LLP (57) ABSTRACT

Anti-viral compounds with low cytotoxicity are identified from screening of products found in Red Sea sponges, including the sponge *Stylissa carteri*. The identified compounds can be brominated pyrrole-2-aminoimidazole alkaloids and derivatives thereof. Specific examples of identified compounds include oroidin, hymenialdisine, and debromohymenialdisine, as well as derivatives thereof. The compounds also can be useful scaffolds or pharmacores for further chemical modification and derivatization. Selected compounds, particularly oroidin, show selective anti-viral HIV-1 activity coupled with reduced cytotoxicity. The compounds can function as HIV reverse-transcriptase inhibitors, and molecular modeling can be used to confirm inhibition.

11 Claims, 8 Drawing Sheets

(56) References Cited

OTHER PUBLICATIONS

Forenza, S., et al., "New bromo-pyrrole derivatives from sponge agelas-oroides". J Chem Soc Chem Comm 1971, 1129-&.

Goh, W.C., et al. "HIV-1 vpr increases viral expression by manipulation of the cell cycle: A mechanism for selection of vpr in vivo". Nat Med 1998, 4, 65-71.

Helfer, M., et al., "The root extract of the medicinal plant pelargonium sidoides is a potent hiv-1 attachment inhibitor". PloS one 2014, 9, e87487.

Hu, Y.W., et al., "Statistical research on the bioactivity of new marine natural products discovered during the 28 years from 1985 to 2012". Mar Drugs 2015, 13, 202-221.

Keifer, P.A., et al., "Bioactive bromopyrrole metabolites from the caribbean sponge agelas-conifera". J Org Chem 1991, 56, 2965-2975.

Kremb, S., et al., "Easy-hit: HIV full-replication technology for broad discovery of multiple classes of HIV inhibitors". Antimicrobial Agents and Chemotherapy 2010, 54, 5257-5268.

Kremb et al: "Aqueous Extracts of the Marine Brown Alga *Lobophora variegata* Inhibit HIV-1 Infection at the Level of Virus Entry into Cells", PLOS One, vol. 9, No. 8, Aug. 21, 2014,p. e103895.

Linington et al: "Latonduines A and B, new alkaloids isolated from the marine sponge *Stylissa carteri*: structure elucidation, synthesis, and biogenetic implications", Organic Letters, American Chemical Society, US, vol. 5, No. 15, Jul. 24, 2003 (Jul. 24, 2003), pp. 2735-2738.

Martinez, J.P. et al., "A. Antiviral drug discovery: Broad-spectrum drugs from nature". Nat Prod Rep 2015, 32, 29-48.

Meijer, L. et al, "Inhibition of cyclin-dependent kinases, gsk-3 beta and ck1 by hymenialdisine, a marine sponge constituent." Chem Biol 2000, 7, 51-63.

Mohammed et al: "Cyclic Heptapeptides from the Jamaican Sponge *Stylissa caribica*", Journal of Natural Products., vol. 69, No. 12, Dec. 1, 2006, pp. 1739-1744.

Newman, D.J. et al., "Therapeutic agents from the sea: Biodiversity, chemo-evolutionary insight and advances to the end of Darwin's 200th year". Diving and Hyperbaric Medicine 2009, 39, 216-225.

O'Rourke, Aubrie Elise, "Bioprospecting of Red Sea Sponges for Novel Anti-Viral Pharmacophores", PhD thesis, King Abdullah University of Science and Technology (2015).

Senthilkumar et al: "Marine Invertebrate Natural Products for Anti-Inflammatory and Chronic Diseases", Evidence-based complementary and alternative medicine : eCAM, vol. 14, No. 2, Jan. 1, 2013, pp. 2334-10.

Sharma, G.M. et al, "Characterization of a yellow compound isolated from the marine sponge phakellia-flabellata". Journal of the Chemical Society—Chemical Communications 1980, 435-436.

(UNAIDS). Global report: Unaids report on the global aids epidemics 2013. JUNPoHA 2013, UNAIDS/ JC2502/1/E.

Yarnold, J.E., et al., "High resolution spatial mapping of brominated pyrrole-2-aminoimidazole alkaloids distributions in the marine sponge *Stylissa flabellata* via maldi-mass spectrometry imaging". Mol Biosyst 2012, 401 8, 2249-2259.

Zidar et al., "Antimicrobial Activity of the Marine Alkaloids, Clathrodin and Oroidin, and Their Synthetic Analogues", Mar. Drugs, 2014, 12, 940-963.

ALKALOIDS FROM SPONGE, SCAFFOLDS FOR THE INHIBITION OF HUMAN IMMUNODEFICIENCY VIRUS (HIV)

CROSS REFERENCE TO RELATED APPLICATION

This is a national stage application of International Application No. PCT/IB2015/002126, filed internationally on Oct. 23, 2015, which claims priority to U.S. Provisional Application Ser. No. 62/068,716, filed on Oct. 26, 2014, both of which are incorporated by reference herein in their entireties.

BACKGROUND

In 2013, there were an estimated 35.3 million people that had been infected and were living with HIV and the number has continued to increase [1]. HIV includes both HIV-1 and HIV-2. Drugs currently used as anti-HIV-1 therapeutics fall under five categories, including inhibitors of viral entry, membrane fusion, the reverse transcriptase, the integrase, and the protease. Highly active anti-retroviral therapy (HAART) combines drugs from at least two of the different classes of the anti-retroviral agents available [2]. Nevertheless, the emergence of drug resistant retroviruses is still a major issue associated with current anti-HIV-1 drug therapies [3]. Hence, the effectiveness of HIV therapy relies on the discovery and approval of novel therapeutics, which are able to combat the various viral replication phases of HIV.

The first anti-retroviral medicine, AZT, was approved in 1987 for the treatment of HIV-1 [4]. This drug terminates DNA strand elongation by the addition of an azide group at the C-3 of the nucleoside sugar. This modification to the 5-carbon sugar is thought to be inspired by the nucleoside analogs produced by the sponge *Tethya crypta*, that possess an arabinose sugar instead of the deoxyribose sugar required for DNA strand elongation [5]. By substituting the groups bound to the 2' and 3' carbons of the nucleoside sugar, a number of HIV-1 reverse transcriptase inhibitors had been generated. This example demonstrates the chemical novelty provided by natural products, which can lead to therapeutic ingenuity. However, the process of finding appropriate natural products can be difficult.

In the past 15 years of clinical trials, it is believed only five novel natural product pharmacophores were investigated in clinical trials. The majority of the 133 naturally derived compounds in clinical trials for the period of 2008-2013 are derivatives of existing pharmacophores that are already present in existing human medicines. For this same time period, only 2 of the 133 compounds, both derivatives of the cyclosporin A pharmacophore, were investigated as anti-viral therapeutic candidates in the treatment of Hepatitis C Virus (HCV) [6]. This reveals that there is a need for novel anti-viral pharmacophores and their derivatives in clinical trials.

A statistical review by Hu et al. [7] illustrates that bioactivities were assigned to only approximately 25% of the marine natural products reported in the literature from 1985-2012. This does not mean that the remaining 75% do not possess bioactivity; instead it suggests a discrepancy between the rate of discovery for marine natural products and the investigation of their associated bioactivities. A further look into the type of bioactivities reported revealed that 56% of the bioactive compounds were associated with anti-cancer activity, but only 3% with anti-viral activity. Interestingly, in years where a greater variety of disease targets were screened in order to identify inhibitors, the proportion of reported bioactivity was the greatest.

This illustrates that there is a need to expand marine natural product screening efforts beyond the detection of anti-cancer activity in order to fully realize the potential utility of marine secondary metabolites.

One Red Sea sponge, *Stylissa carteri*, is known to produce a number of pharmacologically active brominated pyrrole-2-aminoimidazole alkaloids, which are also produced by sponges from the families Agelasidae, Axindellidae, Hymeniacidonidae [8]. A review of the literature showed that the chemical repertoire of *Stylissa* sp. is well characterized with nearly 100 compounds reported. Among these compounds, a dimer of oroidin known as sceptrin along with its derivatives debromosceptrin, dibromosceptrin, and oxysceptrin have been reported to inhibit Herpes Simplex Virus-1 (HSV-1) and Vesicular Stomatitis Virus (VSV) [9]. This lends support to the aim of identifying molecules with anti-viral activity from *S. carteri*. More specific to anti-retroviral activity, another derivative of oroidin, hymenialdisine (HD), has been used experimentally to inhibit Nuclear Factor-kB (NFkB), and subsequently inhibit transcription from the long terminal repeat (LTR) of the Human Immunodeficiency Virus (HIV) in vitro [10].

In a nutshell, while the sponge *Stylissa carteri* is known to produce a number of secondary metabolites displaying anti-fouling, anti-inflammatory, and anti-cancer activity, the anti-viral potential of metabolites produced by *S. carteri* has not been extensively explored or reported.

US Patent Publication 2010/0280004 reports that the chemical structures of latonduine A and esters thereof have been described in the reference, Linington et al. (2003) "Latonduines A and B, New Alkaloids Isolated from the Marine Sponge *Stylissa carteri*: Structure Elucidation, Synthesis, and Biogenetic Implications" *Organic Letters*, 5: 2735.

SUMMARY

Embodiments described herein include, for example, a variety of methods, compositions, and kits.

For example, a first aspect is a method comprising: subjecting crude extracts of *Stylissa carteri* sponge to solid phase extraction to produce a library of fractions; conducting at least one first screening assay of the library of fractions for inhibition of HIV and for cytotoxicity including selecting at least one fraction for further fractionation; fractionating the at least one fraction further to produce at least one additional fraction; conducting at least one second screening assay of the at least one additional fraction for inhibition of HIV and for cytotoxicity, including selecting one or more fractions with decreased cytotoxicity for further identification study; identifying HIV inhibitor molecule candidate(s) based on the inhibition of HIV and decreased cytotoxicity.

In one embodiment, the library of fractions comprises at least four fractions.

In one embodiment, the first screening assay is an HIV replication assay. In another embodiment, the second screening assay is an HIV replication assay. In another embodiment, the first screening assay and the second screening assay are HIV replication assays. In another embodiment, the first screening assay and the second screening assay are HIV-1 replication assays.

In one embodiment, the fractionating is an HPLC fractionating. In another embodiment, the fractionating is an HPLC fractionating which produces at least 11 additional fractions.

In one embodiment, the identifying comprises use of LC-MS. In one embodiment, the identifying comprises determining which molecules appear in multiple fractions. In one embodiment, the identified molecules are further tested with a biochemical assay. In one embodiment, the identified molecules are further tested with a biochemical assay which is a HIV-1 reverse transcriptase assay. In one embodiment, the identified molecules exhibit at least a 50% inhibition of HIV-1 at 7 μM. In one embodiment, the identified molecules exhibit at least a 50% inhibition of HIV-1 at 13 μM. In one embodiment, the identified molecules display at least a 50% inhibition of viral replication at 50 μM with no associated toxicity. In one embodiment, the identified molecules in a biochemical assay inhibit the activity of the HIV-1 reverse transcriptase up to 90% at 25 μM. In one embodiment, the identified molecule is a pyrrole-imidazole alkaloid compound. In one embodiment, the identified molecule is a brominated pyrrole-2-aminoimidazole alkaloid compound. In one embodiment, the identified molecule is oroidin. In one embodiment, the identified molecule is further shown by molecular modeling to inhibit HIV reverse transcriptase.

A second aspect provides for a method for treating a viral infection in a patient, comprising administering to the patient a therapeutically effective amount of a compound, or a pharmaceutically acceptable salt or solvate thereof, which is a brominated pyrrole-2-aminoimidazole alkaloid compound.

In one embodiment, the compound is oroidin or a derivative thereof, hymenialdisine or a derivative thereof, or debromohymenialdisine or a derivative thereof.

In one embodiment, the compound is oroidin or a derivative thereof.

In one embodiment, the patient is infected with an HIV virus. In another embodiment, the patient is infected with an HIV-1 virus.

A third aspect provides for a method for treating a viral infection in a patient, comprising administering to the patient a therapeutically effective amount of a compound, or a pharmaceutically acceptable salt or solvate thereof, which is isolated from a Red Sea sponge.

In one embodiment, the Red Sea sponge is *Stylissa carteri* sponge.

In one embodiment, the patient is infected with an HIV-1 virus.

In one embodiment, the compound is a brominated pyrrole-2-aminoimidazole alkaloid compound. In another embodiment, the compound is oroidin or a derivative thereof.

Other embodiments include use of the compounds described herein, or derivatives thereof (including oroidin and its derivatives) in the manufacture of a medicament and for use of the medicament in treating patients and inhibiting HIV, or more particularly, HIV-1, or HIV reverse transcriptase.

In preferred embodiments, the anti-viral potential of *Stylissa carteri*, in the family Scopalinidae collected from the Red Sea, was investigated. In preferred embodiments, four Solid Phase Extracts (SPE) obtained from *S. carteri* were tested with a well-established cell-based screening system (EASY-HIT, [11]), which evaluates both anti-HIV activity and cytotoxicity. In preferred embodiments, the SPE mixtures were further resolved by high performance liquid chromatography (HPLC) fractionation in order to identify compounds with anti-HIV bioactivity from the Red Sea sponge *S. carteri*.

This led to the initial identification of three previously characterized compounds, i.e. debromohymenialdisine (DBH), hymenialdisine (HD), and oroidin as anti-retroviral molecule candidates. In preferred embodiments, commercially available purified versions of these molecules were re-tested to assess their antiviral potential in greater detail. Specifically, as described more below, DBH and HD exhibit a 50% inhibition of HIV-1 at 7 μM and 13 μM, respectively, but both exhibited cytotoxicity. Conversely, oroidin displayed a 50% inhibition of viral replication at 50 μM with no associated toxicity. Additional experimentation using a biochemical assay revealed that oroidin inhibited the activity of the HIV-1 reverse transcriptase up to 90% at 25 μM.

In sum, *S. carteri* is a sponge with wide geographical distribution that has been shown in preferred embodiments to produce bioactive secondary metabolites, some of which are also present in members of three other sponge families. The three metabolites detected in this study, DBH, HD and oroidin, were characterized previously many years ago. This investigation revealed that these compounds are able to inhibit HIV-1 replication, and can serve as starting scaffolds for further investigation.

Moreover, the long time lag between the original discovery of these compounds and this discovery of their anti-retroviral activity accentuates the unevenness of the screening efforts of natural products and the need for diversification in assay targets. The broader implication of this observation is that the anti-viral pharmacophore potential of many marine natural products might currently be overlooked. Anti-viral screening efforts similar to this one can reveal new marine-derived agents useful in combating these devastating viral diseases.

DETAILED DESCRIPTION

Introduction

US priority provisional application 62/068,716 filed Oct. 26, 2014 is hereby incorporated by reference.

The following PhD thesis is incorporated herein by reference: "Bioprospecting of Red Sea Sponges for Novel Anti-Viral Pharmacophores," Aubrie Elise O'Rourke, 2015, King Abdullah University of Science and Technology, Thuwal, Kingdom of Saudi Arabia; including Chapters 1 and 3 in particular.

References cited herein are incorporated by reference.

In an overview, a Red Sea sponge library is subjected to High Content Screening and anti-viral candidate fractions are identified. Then, in this overview, *Stylissa carteri* is used in the identification of active compounds with respect to HIV and HIV-1.

Marine Sponge

One step in the method is subjecting crude extracts of *Stylissa carteri* sponge to solid phase extraction to produce a library of fractions.

Marine and Red Sea sponges, including *Stylissa carteri*, are generally known in the art. The background and selection of the sponge is described more fully in the incorporated by reference PhD thesis "Bioprospecting of Red Sea Sponges for Novel Anti-Viral Pharmacophores," Aubrie Elise O'Rourke, 2015, King Abdullah University of Science and Technology, Thuwal, Kingdom of Saudi Arabia.

The particular sponge, such as *Stylissa carteri*, can be selected out of a plurality of different sponges based on, among other factors, a high content screening approach.

The Red Sea is a unique sampling environment. For example, it exhibits high temperature and salinity in opposing gradients. Areas of the Red Sea can be genetically distinct from the Indian Ocean, and can provide distinct environmental conditions within the Red Sea. Libraries of Red Sea sponges can be established covering 15 or more distinct sponges, covering 15 or more genera, covering two or more classes (including Demospongiae and Calcarea), including 1-8 replicates per sponge, and in some cases identification by spicules.

Solid Phase Extraction (SPE)

Solid phase extraction (SPE) as a pre-fractionation step is generally known in the art and described more below in the working examples. Also, background for SPE and SPE itself are described more in the incorporated by reference PhD thesis "Bioprospecting of Red Sea Sponges for Novel Anti-Viral Pharmacophores," Aubrie Elise O'Rourke, 2015, King Abdullah University of Science and Technology, Thuwal, Kingdom of Saudi Arabia; including Chapters 1 and 3 in particular.

The SPE can produce a library of fractions, and the library of fractions can comprise at least two, at least three, at least four, at least five, or more fractions.

The sponge can be ground in liquid nitrogen and placed in methanol and then dried to HP20SS for SPE. Multi-step elution can be carried out using increasing polarity in water-isopropanol mixtures and then using methanol. The eluted materials can be subjected to centrifugal evaporation, and fractions can be redissolved in, for example, methanol.

High Content Screening (HCS) can be carried out. For example, fractions can be clustered to a reference library based on shared phenotypic profiles ("fingerprinting"). Pre-fractionated marine extracts can be used. An example of a well-characterized reference library of pharmaceutically active single molecule compounds is LOPAC1280). The compounds can cluster according to a shared mechanism of action. This can provide a prediction for the structure class and/or mechanism of action for the compounds of a pre-fractionated sponge mixture.

Screening, Assays

Another step provides for conducting at least one first screening of the library of fractions for inhibition of HIV and for cytotoxicity in a first assay including selecting at least one fraction for further fractionation. In some cases, at least two fractions, or at least three fractions, or at least four fractions, or at least five fractions can be selected for further fractionation. In the meantime, the selected fractions can be subjected to a first assay which is an HIV replication assay, or more specifically an HIV-1 replication assay.

Screening and assays are generally known in the art. They are also described more in the PhD thesis which is incorporated herein by reference: "Bioprospecting of Red Sea Sponges for Novel Anti-Viral Pharmacophores," Aubrie Elise O'Rourke, 2015, King Abdullah University of Science and Technology, Thuwal, Kingdom of Saudi Arabia; including Chapters 1 and 3 in particular. See also references cited hereinbelow including references 11-12 to Kremb et al.

Cell based assays are generally known in the art including anti-viral assays, HIV replication assays, and HIV-1 replication assays. One wants to maximize inhibition of the viral target while also minimizing or eliminating cytotoxicity.

The so-called "EASY-HIT" screening technology can be used. This is a technology that uses LC5-RIC cells, a HIV-1 permissive HeLa-derived cell line with a stable fluorescent reporter gene activated by HIV Tat and Rev proteins.

US Patent Publication No. 2003/0181375 describes a cell-based HIV assay.

Fractionation and More Screening

Another step provides for fractionating the at least one fraction further to produce at least one additional fraction. Fractionation is generally known in the art. In one embodiment, the fractionation is a chromatographic based fractionation, such as an HPLC fractionation. The fractionating can produce, for example, at least 3, or at least 5, or at least 7, or at least 10, or at least 11 additional fractions.

Also provided for is conducting at least one second screening of the at least one additional fraction for inhibition of HIV and for cytotoxicity in a second assay, including selecting one or more fractions with decreased cytotoxicity for further identification study. This second screening can be essentially the same as the first screening, described above. The second screening also can be targeted for HIV and HIV-1.

In one embodiment, the second assay is an HIV replication assay. In another embodiment, the first assay and the second assay are HIV replication assays, and in particular, can be HIV-1 replication assays. Again, so-called "EASY-HIT" screening technology can be used for the second assay.

Identification of Molecules, Further Testing

Another step provides for identifying HIV inhibitor molecule candidate(s) based on the inhibition of HIV and decreased cytotoxicity.

The identification can be carried out by known methods such as chromatography and/or mass spectral analysis. In one embodiment, the identifying comprises use of LC-MS (liquid chromatography-mass spectroscopy). In one embodiment, the identifying comprises determining which molecules appear in multiple fractions. This can be done by overlaying traces on each other, for example.

In one embodiment, the identified molecules are further tested with a biochemical assay. In another embodiment, the identified molecules are further tested with a biochemical assay which is a HIV-1 reverse transcriptase assay.

If the identified molecules are known, then they can be purchased or prepared by methods known in the art, and subjected to further testing to confirm that the compounds isolated from the sponge are the same.

Inhibition of HIV-1 is one useful test, and a particular concentration can be selected for the test. For example, in one embodiment, the identified molecules exhibit at least a 25%, or at least a 50%, or at least a 75% inhibition of HIV-1 at 7 µM. In another embodiment, the identified molecules exhibit at least a 25%, or at least a 50%, or at least a 75% inhibition of HIV-1 at 13 µM.

In another embodiment, the identified molecules display at least a 25%, or at least a 50%, or at least a 75% inhibition of viral replication at 50 µM with no associated toxicity.

In addition to cell testing, biochemical testing or assays also can be carried out for HIV and HIV-1 inhibition. The assay can be done with respect to activity and inhibition for HIV-1 reverse transcriptase. For example, in one embodiment, the identified molecules in a biochemical assay inhibit the activity of the HIV-1 reverse transcriptase up to 30%, or up to 60%, or up to 90% at 25 µM.

The identified molecule can be a pyrrole-imidazole alkaloid compound. In one embodiment, the identified molecule is a brominated pyrrole-2-aminoimidazole alkaloid compound.

In one particular embodiment, the identified molecule is oroidin, and the 10Z-Hymenialdisine and debromohymenialdisine molecules are excluded (due to higher levels of cytotoxicity). The oroidin molecule or compound is known in the art. See, for example, U.S. Pat. Nos. 5,834,609; 7,098,204; and 7,838,681. It can be purchased commercially and its activity can be verified. The oroidin structure is:

clathrodin (R = H)
oroidin (R = Br)

Oroidin does not have the seven membered lactam ring as found in 10Z-Hymenialdisine and debromohymenialdisine. Rather, it has a central linear propenyl group which links together the terminal 2-aminoimidazole group and the terminal carboxyamide brominated pyrrole ring. The structure of 10Z-Hymenialdisine, having the seven member lactam ring, is shown:

Aso, the structure of debromohymenialdisine, also having the seven member lactam ring, is also shown:

Derivatives and synthetic analogs of identified compounds such as oroidin can be prepared as known in the art. For example, side chains or functionalities can be introduced. Modification can be carried out on the pyrrole ring or on the pyridinium ring, for example. Another example for derivatizing is described in, for example, Zidan et al., *Mar. Drugs,* 2014, 12, 940-963. WO 01/041768 describes hymenialdisine and derivatives thereof.

Derivatives can include the pharmaceutically acceptable salts. Acid addition salts can be formed with organic or inorganic acids. Examples of acids include acetic, ascorbic, maleic, phosphoric, salicylic, and/or tartric acids.

In addition, molecular modeling can be carried out as known in the art to evaluate and help confirm the mechanism of the anti-viral activity. For example, AutoDock software can be used, and the binding of molecules identified herein, such as oroidin, to HIV RT can be modeled. The modes of binding in a binding pocket can be evaluated, and the energy of the modes of binding can be evaluated. Hydrophobic binding pockets can be reviewed. Molecular modeling is also described more in the PhD thesis which is incorporated herein by reference: "Bioprospecting of Red Sea Sponges for Novel Anti-Viral Pharmacophores," Aubrie Elise O'Rourke, 2015, King Abdullah University of Science and Technology, Thuwal, Kingdom of Saudi Arabia; including Chapters 1 and 3 in particular.

The combination of an assay such as EASY-HIT, in combination with High Content cytological profiling, as well as molecular modeling can provide the best guidance for discovering new applications of known and unknown compounds.

Kits can be provided to execute the steps and methods described herein. Instructions can be provided with the kits.

The screening steps and methods described herein can be used to produce pharmacologically active compounds which can be used to treat patients, particularly those that have a viral infection, or particularly those that have an HIV infection, or particularly those that have an HIV-1 infection. The compounds can be formulated as needed with one or more ingredients for its use in such patients as known in the art, so the identified compounds, or derivatives thereof, can be considered as an active pharmaceutical ingredient (API).

Methods of Treating Patients

The descriptions provided herein can be used in methods of treating patients. One aspect provides for a method for treating a viral infection in a patient, comprising administering to the patient a therapeutically effective amount of a compound, or a pharmaceutically acceptable salt thereof, which is a brominated pyrrole-2-aminoimidazole alkaloid compound.

In one embodiment of this method, the compound is oroidin or a derivative thereof, hymenialdisine or a derivative thereof, or debromohymenialdisine or a derivative thereof. In one embodiment, the compound is oroidin or a derivative thereof.

In one embodiment, the patient is infected with an HIV virus, whereas in another embodiment, the patient is infected with an HIV-1 virus.

Still further, another embodiment provides for a method for treating a viral infection in a patient, comprising administering to the patient a therapeutically effective amount of a compound, or a pharmaceutically acceptable salt thereof, which is isolated from a Red Sea sponge. The Red Sea sponge, in one embodiment, is *Stylissa carteri* sponge.

In one embodiment, the patient is infected with an HIV virus such as the HIV-1 virus.

In one embodiment, the compound is a brominated pyrrole-2-aminoimidazole alkaloid compound. In another embodiment, the compound is oroidin or a derivative thereof.

The therapeutically effective amount can be optimized and adapted, of course, to many particular uses including regulatory factors, delivery methods, and a host of other factors. In another embodiment, the therapeutically effective amount is provided in the form of a solid having an amount of active ingredient of at least 1 wt. %. In another embodiment, the therapeutically effective amount is provided in the form of a solid having an amount of active ingredient of at least 5 wt. %. A single does in some cases provides for 100 to 1,000 mg, or 250 to 750 mg per unit dosage form. Dosage can be, for example, 1 to 4 times per day.

Pharmaceutically acceptable carriers can be used. The carrier can be, for example, solid or liquid depending on the administration form. Administered forms include, for example, parentally, rectally, topically, transdermally, or orally. Injectable routes can be used. Oral routes can include lozenges, compressed tablets, pills, tablets, capsules, drops, syrups, suspensions, or emulsions. Solid oral dosage forms can be used.

In one embodiment, the identified compound is not in a salt form. In another embodiment, the identified compound is in the form of a pharmaceutically acceptable salt as known in the art. In one embodiment, the identified compound is not in a solvate form. In another embodiment, the identified compound is in the form of a pharmaceutically acceptable solvate as known in the art. The term pharmaceutically acceptable solvate comprises the hydrates and the solvent addition forms that compounds described herein can form. Examples of such forms are e.g. hydrates, alcoholates, e.g. methanolates, ethanolates and propanolates, and the like. Particular solvates are the ethanolate, e.g. the monoethanolate.

In general, the identified compound can be in a variety of forms including salts, stereoisomeric forms, racemic mixtures, prodrugs, esters, solvates, derivatives, or metabolites thereof.

The term "prodrug" is known in the art and means the pharmacologically acceptable derivatives such as, for example, esters, amides and phosphates, such that the resulting in vivo biotransformation product of the derivative is the active drug as described herein. Prodrugs of a compound are prepared by modifying functional groups present in the compound in such a way that the modifications are cleaved, either by routine manipulation or in vivo, to the parent compound. Prodrugs are often characterized by excellent aqueous solubility, increased bioavailability and are readily metabolized into the active inhibitors in vivo.

The compounds described herein can inhibit the HIV reverse transcriptase and may also inhibit reverse transcriptases having similarity to HIV reverse transcriptase. Such similarity may be determined using programs known in the art including BLAST. In one embodiment, the similarity at the amino acid level is at least 25%, interestingly at least 50%, more interestingly at least 75%. In another embodiment, the similarity at the amino acid level at the binding pocket, for the compounds of the present invention is at least 75%, in particular at least 90% as compared to HIV reverse transcriptase. Compounds described herein can be tested in other lentiviruses besides HIV-1, such as, for example, SIV and HIV-2.

Another embodiment provides that the composition consists essentially of, or consists of, an isolated and purified form of the identified compound, or a pharmaceutically acceptable salt thereof.

Treatment can comprise use of combinations of APIs including inhibitors of HIV RT and protease inhibitors. HIV inhibitors are generally known and categories include NRTIs, NNRTIs, NtRTIs, PIs, and fusion inhibitors. See, for example, US Patent Publication Nos. 2014/0142174 and 2007/0249655. Triple combinations can be used. The pharmaceutical drugs can be taken simultaneously or in sequence.

Preferred Embodiments and Working Examples

Additional preferred embodiments, including working examples, are provided below.

1.1. Inhibition of HIV-1 replication by S. carteri Solid Phase Extract (SPE) fraction 1

Three biological replicates of S. carteri specimens were collected from different coral reefs in the Red Sea and were pre-fractionated by Solid Phase Extraction (SPE) and subsequently evaluated for anti-HIV activity and cytotoxicity in the EASY-HIT system. SPE fractionation was performed in order to obtain desalted fractions that were enriched for pharmacologically relevant small organic compounds with differing polarities. This was achieved by extracting a portion of the sponge sample with methanol overnight, then drying the extracted material to HP20SS beads. The beads were loaded onto a flash cartridge and eluted with 25% IPA/H20 (SPE F1), 50% IPA/H20 (SPE F2), 75% IPA/H20 (SPE F3), 100% MeOH (SPE F4). The eluates were concentrated to a pellet, weighed, and re-eluted in methanol for subsequent testing.

Figure 1:
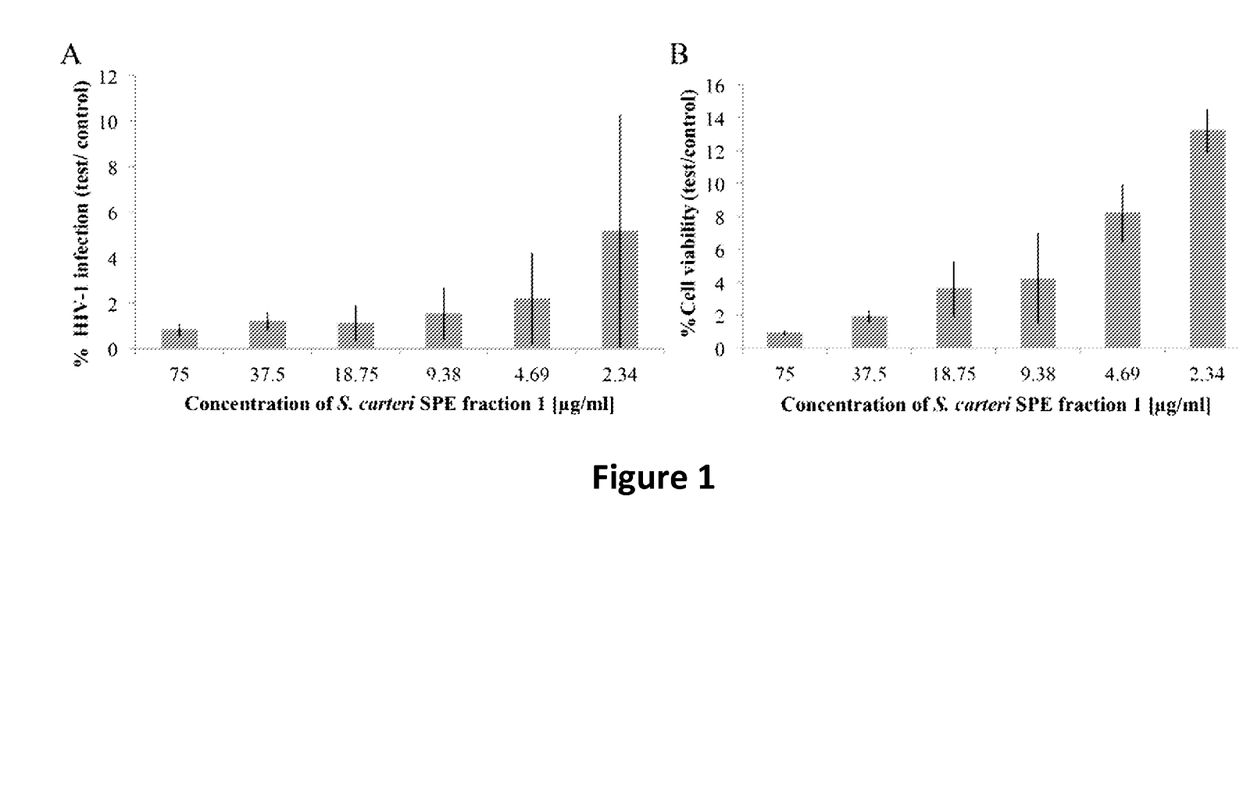
FIG. 1. (A) Three biological replicates of *S. carteri* SPE F1 were each tested for the ability to inhibit HIV-1 infection of HIV-1 permissive LC5-RIC reporter cells in the EASY-HIT assay; (B) Vitality of the infected LC5-RIC cells treated with three biological replicates of *S. carteri* SPE F1 and assessed by the MTT assay. The error bars represent one standard deviation from the mean. P values between the six tested concentrations for SPE F1 for the % infection and % viability are P=0.2738 and P=0.0001, respectively.
Figure 6:
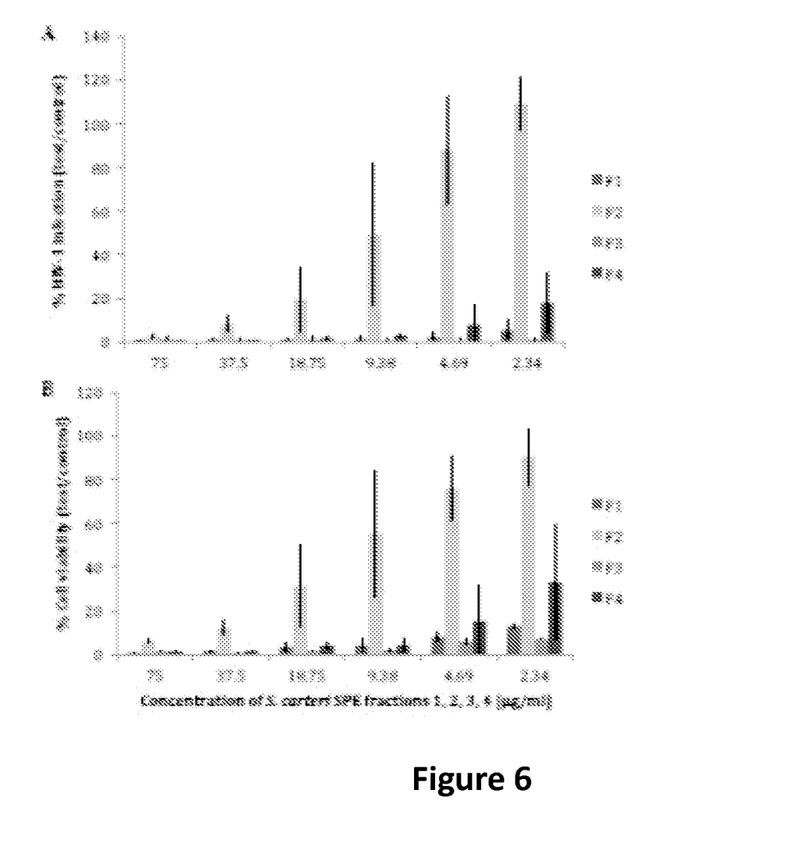
FIG. 6. (A) Three biological replicates of *S. carteri* SPE fraction 1, 2, 3, 4 were each tested for the ability to inhibit HIV-1 infection of HIV-1 permissive LC5-RIC reporter cells in the EASY-HIT assay at six concentrations; (B) Vitality of the infected LC5-RIC cells treated with three biological replicates of *S. carteri* SPE fractions 1, 2, 3, 4 at six concentrations and assessed by the MTT assay. Error bars represent one standard deviation from the mean. The P values between the six tested concentrations for each SPE fractions are as follows (reported first for the % infection and then % viability): F1, P=0.2738, p=0.0001; F2, P=0.0001, P=0.0001; F3, P=0.1531, P=0.0001; F4, P=0.0556, P=0.0629.

When tested on the cell-based HIV-1 replication assay, SPE fraction 1 (SPE F1) was observed to display the strongest inhibitory effect with the least amount of confounding toxicity (FIG. 6). This inhibition by S. carteri SPE fraction 1 (SPE F1) occurs in the early phase of HIV-1 replication, which suggests inhibition of events in the virus replication cycle that include viral entry, fusion, reverse transcriptase, and HIV-1 integration. The HIV-1 permissive LC5-RIC reporter cells, when treated with serial dilutions from three biological replicates of S. carteri SPE F1, displayed less than 1-12% infected cells at concentrations as low as 2.34 µg/ml (FIG. 1a).

However, these fraction replicates also showed clear effects on the metabolic activity of cells determined by MTT assay (FIG. 1b), which is often used as a parameter of cell viability. A caveat in regard to cell-based assays is that cytotoxic compounds will reduce overall cell numbers and as a result the overall reporter expression will also be reduced. If effects on reporter expression are viewed without cell viability data, this can lead to a false positive hit. Conversely, when screening mixtures with a cell-based assay, a mixture which harbors effective compounds can be overlooked during screening and ruled out on account of the one or more cytotoxic compounds that mask the activity of the effective compound lending to false negatives.

However, the EASY-HIT assay, which has been validated previous to this study [11-13], provides a robust platform to determine whether antiviral and cytotoxic activities of SPE fraction 1 are separable entities by further resolving the chemical constituents of the extract mixture and retesting of these fractions. To this end, SPE F1 was subjected to further orthogonal HPLC separation steps and the ensuing fractions were again tested for the desired anti-retroviral bioactivity.

1.2. Biological Activities of HPLC Fractions Derived from S. carteri SPE Fraction 1

Figure 2:
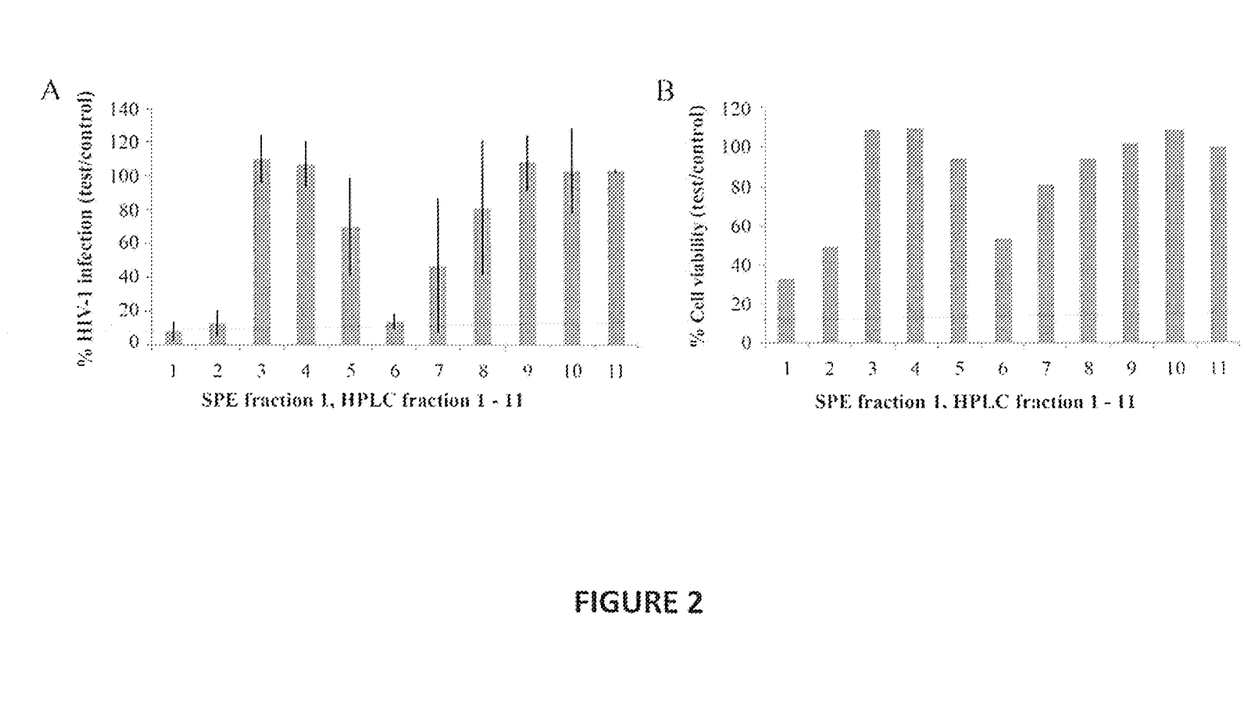
FIG. 2. (A) HIV infection of RIC cells: Three biological replicates of 11 HPLC fractions (approx. 20 μg/ml each) generated from *S. carteri* SPE F1 were tested for the ability to inhibit HIV-1 replication in the EASY-HIT assay; (B) The vitality of the infected LC5-RIC reporter cells treated with the three biological replicates of HPLC fraction 1-11 generated from *S. carteri* SPE F1 were assess by the MTT assay. The error bars represent one standard deviation from the mean. P values between the 11 tested HPLC fractions for the % infection and % viability are P=0.0001 and P=0.0001, respectively.

The three biological replicates of the parent SPE F1 were further fractionated into 11 HPLC fractions using an XDB-C18 column. The fractions were subsequently tested for the ability to inhibit HIV-1 replication in the EASY-HIT assay similar to the SPE fraction. In this experimentation, it was found that HPLC fractions 1, 2, and 6 are capable of inhibiting HIV-1 replication up to 90% (FIG. 2a); cell vitality testing of the HIV-1 permissive LC5-RIC reporter cells treated with HPLC fractions 2 and 6 showed a cell vitality of 50%, but with HPLC fraction 1 it was reduced to 33%. Consequently, only fractions 2 and 6 were considered for further studies (FIG. 2b).

Figure 3:
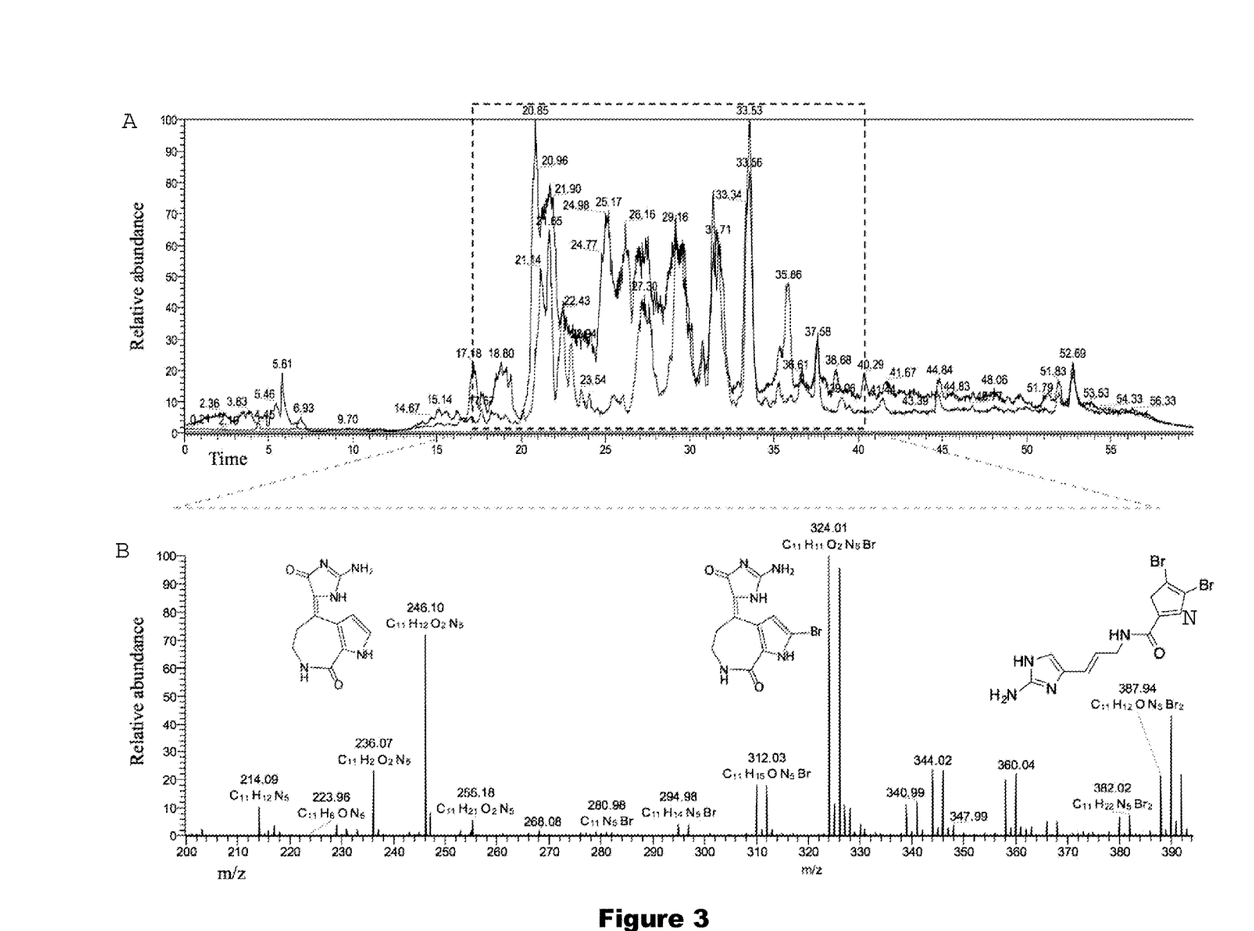
FIG. 3. (A) Overlay of LC-MS chromatograms for HPLC fractions 2 (black) and 6 (red) generated from *S. carteri* SPE fraction 1; and (B) a spectrum of the m/z values common to both HPLC fraction 2 and 6 between minutes 17-40. The three known compounds 164 debromohymenialdisine (m/z [M+H]+ 246, $C_{11}H_{12}N_5O_2$), 10Z-hymenialdisine (m/z [M+H]+ 324, $C_{11}H_{11}BrN_5O_2$), oroidin (m/z [M+H]+ 389, $C_{11}H_{12}Br_2N_5O$) have the greatest relative abundance among the shared compounds common to both HPLC fractions 2 and 6.

1.3. Identification of HIV-1 Candidate Inhibitors in Bioactive S. carteri HPLC Fractions 2 and 6 by Overlay of Liquid Chromatography-Mass Spectrometry (LC-MS) Spectra In order to identify the compounds responsible for the HIV inhibitory activity, HPLC fractions 2 and 6 resulting from SPE F1 were analyzed by LC-MS. The compounds common to the two fractions were assumed to be candidates for anti-viral compounds (FIG. 3a). The most prominent compounds in the spectra included: debromohymenialdisine (DBH, m/z [M+H]+ 246, $C_{11}H_{12}N_5O_2$), hymenialdisine (HD, 10Z-hymenialdisine (m/z [M+H]+ 324, $C_{11}H_{11}BrN_5O_2$), and oroidin (m/z [M+H]+ 389, $C_{11}H_{12}Br_2N_5O$) (FIG. 3b).

Figure 4:
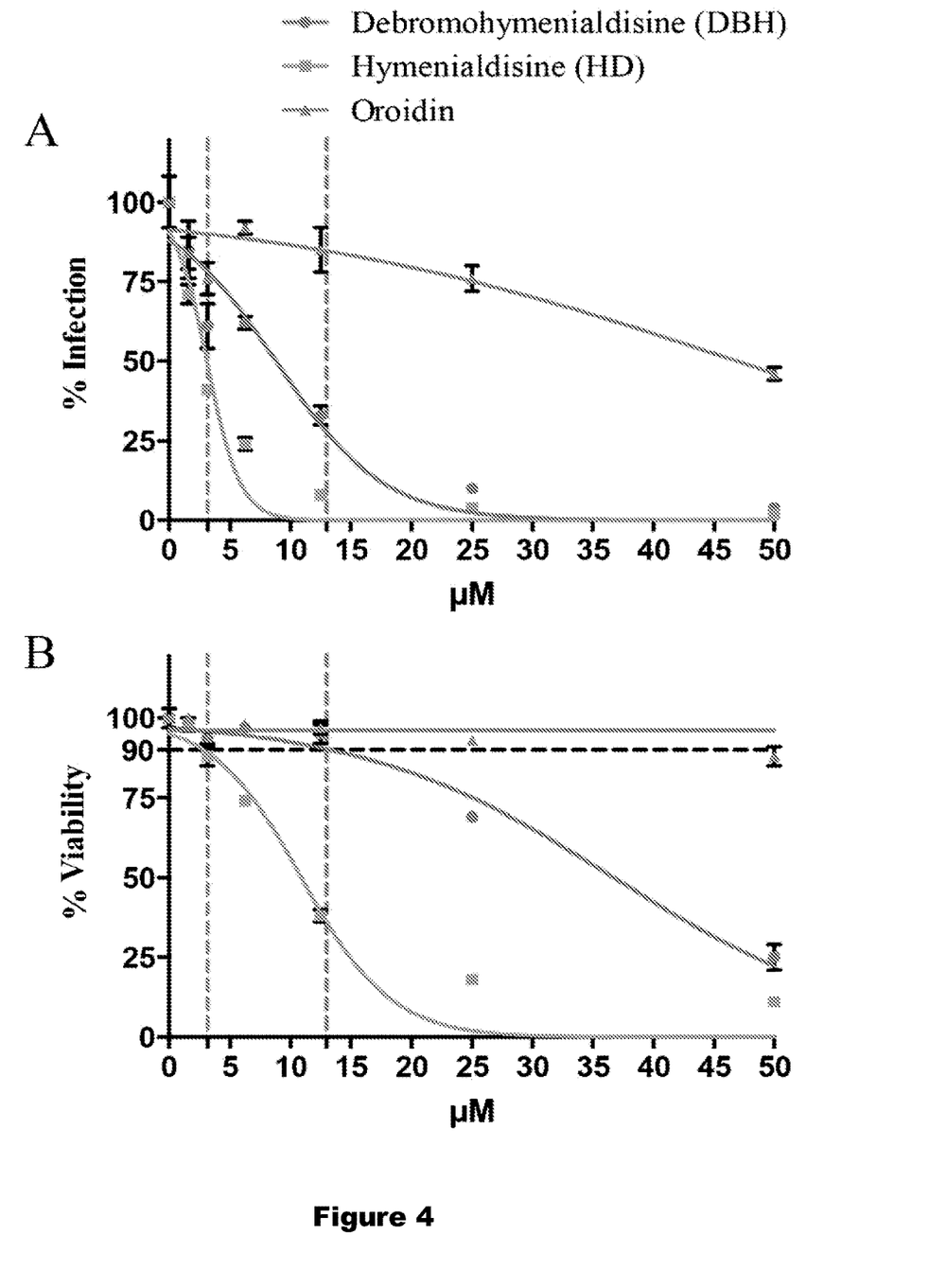
FIG. 4. (A) The single compounds DBH, HD, and oroidin from *S. carteri* are tested for the ability to inhibit HIV-1 replication in HIV-1 permissible LC5-RIC reporter cells in the EASY-HIT assay; (B) Vitality of the infected LC5-RIC reporter cells treated with the single compounds DBH, HD, and oroidin from *S. carteri* was assessed by the MTT cell proliferation assay. The error bars represent one standard deviation from the mean. The P values between the 6 tested concentrations of each of the three compounds are reported first for the % infection and then % viability graph as follows: debromohymenialdisine, P=0.0001, P=0.0001; hymenialdisine, P=0.0001, P=0.0001; oroidin, P=0.0001, P=0.0001.
Figure 7:
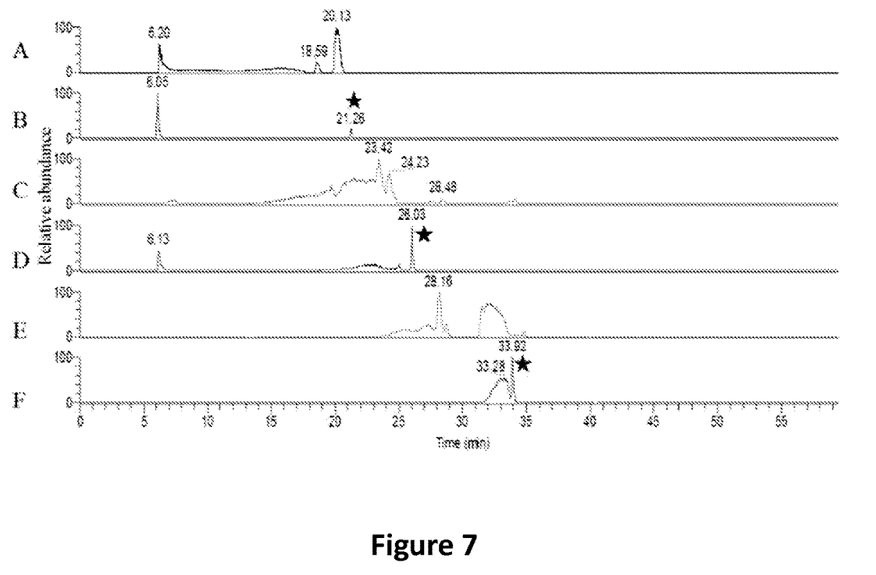
FIG. 7. LC-MS chromatograms (extracted ion chromatograms) of the m/z ions associated with debromohymenialdisine, hymenialdisine, and oroidin for SPE fraction 1 from *S. carteri* and comparison to the purchased standards. (A) retention time for debromohymenialdisine in the SPE fraction 1 of *S. carteri*. (B) retention time for the debromohymenialdisine standard (starred). (C) retention time for hymenialdisine in the SPE fraction 1 of *S. carteri*. (D) retention time for the hymenialdisine standard (starred). (E) retention time for oroidin in the SPE fraction 1 of *S. carteri*. (F) retention time for the oroidin standard (starred).
Figure 8:
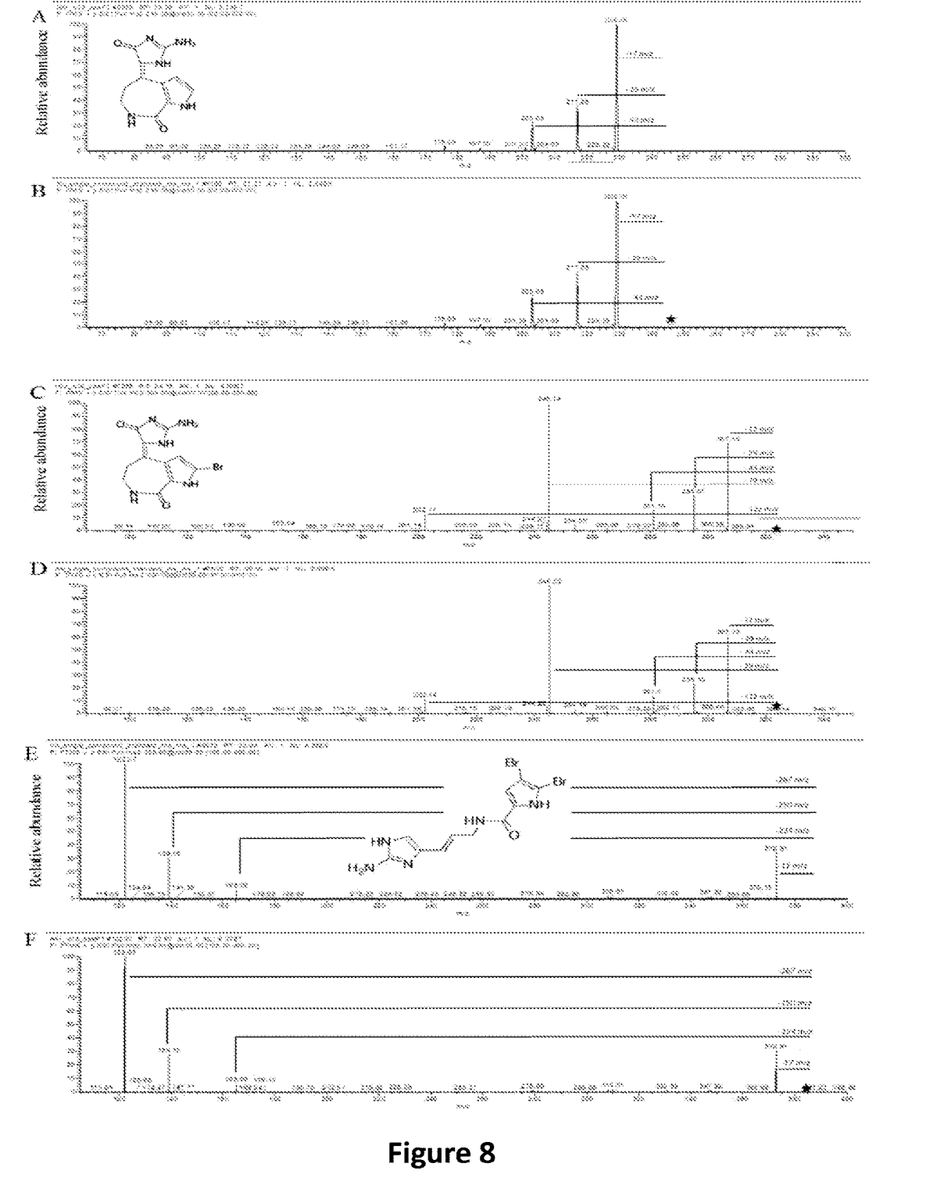
FIG. 8. MS/MS fragmentation pattern for debromohymenialdisine, hymenialdisine, and oroidin using a collision-induced dissociation of 30 eV. (A) Fragmentation pattern of debromohymenialdisine in the SPE fraction 1 of *S. carteri*. (B) Fragmentation pattern of the debromohymenialdisine standard. (C) Fragmentation pattern of hymenialdisine in the SPE fraction 1 of *S. carteri*. (D) Fragmentation pattern of the hymenialdisine standard. (E) Fragmentation pattern of oroidin in the SPE fraction 1 of *S. carteri*. (F) Fragmentation pattern of the oroidin standard.

1.4. Three HIV-1 Candidate Inhibitors Hymenialdisine, Debromohymenialdisine, and Oroidin From S. carteri Inhibit HIV-1 Replication to Varying Degrees Oroidin [14], HD and DBH [15,16], isolated and characterized in 1973 and the 1980s, respectively, have since been synthesized and are available for purchase. The single compounds were purchased and evaluated in the EASY-HIT assay for their ability to inhibit HIV-1 replication. The pure compounds were also used as standards and their presence was confirmed in the SPE F1 from the Red Sea S. carteri specimen collected in this study. Tandem mass spectrometry showed a similar retention time and fragmentation pattern for authentic DBH, HD, and oroidin and their corresponding compound present in the Red Sea S. carteri SPE F1 (FIGS. 7 and 8). The DHB treatment inhibited HIV-1 infection down to 30% of untreated controls at a concentration of 13 µM without affecting cell vitality. (FIG. 4 a, b). The specific antiviral effect was even stronger for HD, which clearly inhibited HIV infection to <40% at a concentration of 3.1 µM without affecting cell vitality. Oroidin showed the weakest antiviral activity, reducing HIV-1 infection to 50% at a concentration of 50 µM, and proved to be nontoxic for cells at all tested concentrations (FIG. 4 a,b).

These results support the idea that the SPE F1 contains different compounds with anti-viral activities. This includes compounds with both weak but selective anti-viral activities (e.g. oroidin) and other compounds that show stronger antiviral activities but may also affect vitality of cells at higher concentrations.

Figure 5:
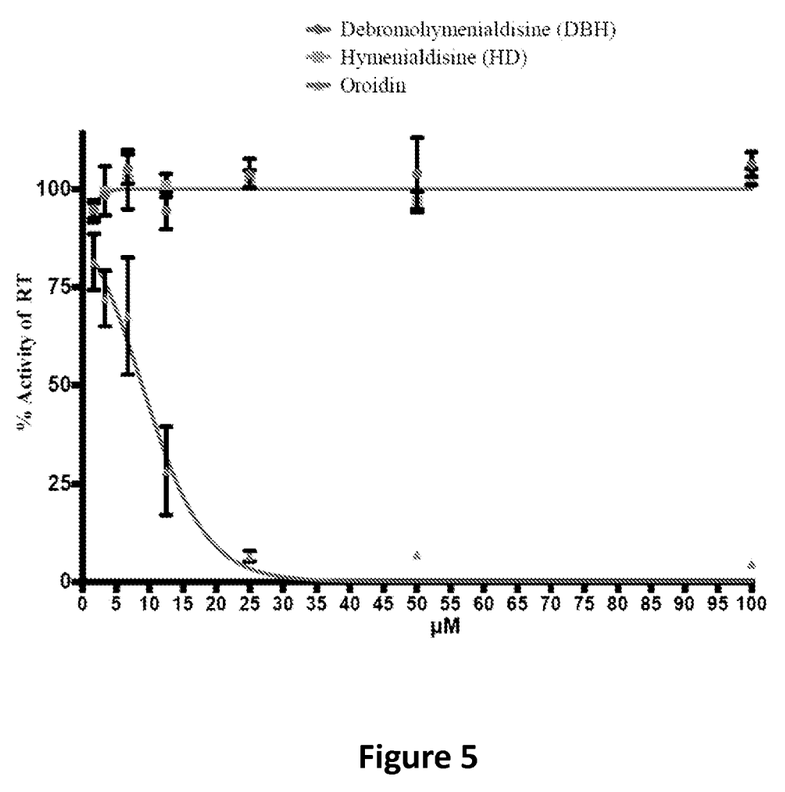
FIG. 5. Inhibitory activity of DBH, HD and oroidin from *S. carteri* on the HIV-1 RT in a biochemical assay. The error bars represent one standard deviation from the mean. The P values between the 11 tested HPLC fraction are reported for % activity of the RT as follows: debromohymenialdisine, P=0.0023; hymenialdisine, P=0.169; oroidin, P=0.0001.

1.5. Oroidin from S. carteri inhibits the HIV-1 Reverse Transcriptase (RT) in a Biochemical Assay The procured purified preparations of DBH, HD, and oroidin were screened in an HIV-1 RT biochemical assay. Interestingly, DBH and HD did not show anti-HIV-1 RT activity. In contrast, oroidin was capable of a 90% inhibition of the HIV-1 RT enzyme at concentrations greater than 25 µM (FIG. 5). Whereas, in the cell-based experimentation presented here, oroidin was shown to reduce HIV-1 replication in a cell-based assay up to 50% when applied at a 50 µM concentration and was non-cytotoxic at all tested concentrations. This suggests that the mechanism of inhibition of oroidin as an HIV-1 RT inhibitor might be hindered by its poor ability to be absorbed by a living cell. Thus improvements in oroidin as a prospective scaffold for HIV-1 inhibition would require additional medical chemistry modification.

The findings are in contrast to a previous study where oroidin was obtained as a by-product and was tested for its ability to inhibit HIV replication. In that study, oroidin was found inactive, but also non-cytotoxic. The previous study [17] did not detail the concentrations used in the assay; however, their negative result may have been due to testing at too low a concentration of oroidin to observe activity in a cell-based assay.

Many of the pharmacologically active brominated pyrrole-2-aminoimidazole alkaloids from *S. carteri* are assumed to be derivatives of the building block oroidin [18]. In this study, oroidin was found to be capable of inhibiting HIV-1 replication without causing cytotoxicity. HD, a derivative of oroidin, was also found to be capable of inhibiting HIV-1 replication; however, cytotoxicity was observed at concentrations greater than 3.1 µM. This could be due to the ability of HD to bind Nuclear Factor-kB (NFkB), which is crucial for a number of cellular processes as well as the ability to induce the process of transcription from the HIV-1 long terminal repeat (LTR). Similarly, DBH gives rise to cytotoxicity at concentrations greater than 13 µM, a value greater than that observed for HD, perhaps on account of HD's lack of the electronegative bromine atom. Furthermore, HD along with DBH have been reported to compete with ATP for binding to a number of cyclin-dependent kinases (CDK), including CDK2 [19], where the ability to inhibit CDK2 has been shown to decrease the transcription of the HIV-1 virus [18,20]. Additionally, DBH and HD have been reported to abrogate the G2-checkpoint of the cell cycle [21]. A G2 arrest is thought to pose a replicative advantage for the virus, as the HIV-1 LTR is most active during this phase [22]. This suggests that DBH and HD may also be able to relieve the cell cycle arrest that supports HIV pathogenesis. However, a prolonged arrest can also lead to apoptosis and result in cytotoxicity. NFkB, CDK2, and G2-checkpoint interference are three possible mechanisms of action to explain the inhibition observed from HD and DBH in this study. However, the inhibition of such ubiquitous cellular proteins and processes could also explain the cytotoxicity associated with HD and DBH as well as that observed for the parent SPE F1 mixture and in HPLC fractions 1, 2 and 6.

From this study, it was observed that oroidin is directly acting to inhibit the retroviral reverse transcriptase, while DBH and HD do not affect this enzyme. It remains to be determined whether DBH and HD possess anti-viral activity at other steps of the virus life cycle that were not measured in this study. One can assess whether oroidin only affects the reverse transcriptase or whether potential other enzymes or life cycle steps are affected.

Experimental Section 2.1. *S. carteri* Specimen Collection and Sample Fractionation Three biological replicates of *S. carteri* (described by Denny 1889, identified by Dr. N. J. de Voogd) were collected using gardening sheers from three coral reef locations: C26 from Inner Fsar, West (22° 13.974 N, 39° 01.760 E), C14 from Inner Fsar, East (22° 13.850 N, 39° 02.216 E), and D5 from Al Fahal, East (22° 15.119 N, 38° 57. 761 E), using SCUBA at approximately 12 meters depth. The specimens were washed with 1% Phosphate Buffered Saline (PBS) on the boat then wrapped in foil and placed on ice then stored at −80° C. until processing. Small sponge specimens of 4-10 grams of sponge specimen were ground using a mortar and pestle and then extracted with 15 ml of methanol overnight at 4° C. The following day, the methanol extract was dried onto 150 mg of Diaion HP20SS beads in a CentriVap complete vacuum concentrator (Labconco, Kansas City, USA) on low and the beads were then loaded into a 25 ml Flash Cartridge (Sorbtech, Norcross, Ga.) with 0.795 diameter Frits (Sorbtech, Norcross, Ga.), desalted with deionized water (15 ml, FW1, FW2) and then eluted with 15 ml of each solvent in the following series: 25% IPA/H2O (SPE fraction 1), 50% IPA/H2O (SPE fraction 2), 75% IPA/H2O (SPE fraction 3), 100% MeOH (SPE fraction 4) [23]. The solvents were centrifugally evaporated in a CentriVap complete vacuum concentrator (Labconco, Kansas City, Mo.) and re-dissolved in 2 ml HPLC grade methanol (Sigma Aldrich) for injection into the HPLC.

2.1.1 Analytical Chemistry of Bioactive *S. carteri* Fractions

The HPLC fractionation was peak-based and was carried out with a 50 µl (approximately 500 µg of material, dry weight) injection of material and a flow rate of 0.400 ml/min using a ZORBAX Eclipse XDB-C18 LC Column, 4.6 mm, 150 mm, 5 µm (Agilent Technologies, Santa Clara, Calif., USA), and the gradient reported in Table 1. SPE fraction 1 and HPLC fractions 2 and 6 were analyzed on the Thermo LTQ Orbitrap with 10 µl of material and a flow rate of 0.800 ml/min using a ZORBAX Eclipse XDB-C18 LC Column, 4.6 mm, 150 mm, 5 µm and the gradient reported in Table 2. Analysis and prediction of elemental formulas were carried out with Xcalibur 2.1 software (Thermo Scientific). MS/MS was performed using a CID of 30 eV on both the parent SPE fraction 1 as well as the three standards of DBH, HD and oroidin and targeted m/z 246.09, 324.00, and 389.93, respectively.

2.1.2 Single Compounds From Bioactive *S. carteri* Fractions

The individual synthesized compounds debromohymenialdisine were obtained from Enzo Life Sciences, PA, USA (Lot: L20314), 10Z-hymenialdisine (Lot: L27315) and oroidin (Lot: L26427) and product information is as follows:

| Debromohymenialdisine | |
|---|---|
| Alternative Name: | DBH, 4-(2-Amino-4-oxo-2-imidazolin-5-ylidene)-4,5,6,7- tetrahydropyrrolo[2,3-c]azepin-8-one |
| IDENTITY: | Identity determined by $^1$H-NMR and MS. |
| FORMULA: | $C_{11}H_{11}N_5O_2$ |
| MW: | 245.2 |
| PURITY: | 95% (HPLC) |
| APPEARANCE: | Yellow solid. |
| CAS: | 75593-17-8, 125118-55-0 |
| SOURCE/HOST: | Isolated from sponge *Axinella carteri*. |
| SOLUBILITY: | Soluble in 100% ethanol or DMSO. |
| STORAGE: | −20° C. |
| HANDLING: | Keep under inert gas. Protect from light. |
| Hymenialdisine | |
| IDENTITY: | Identity determined by $^1$H-NMR and MS |
| FORMULA: | $C_{11}H_{10}BrN_5O_2$ |
| MW: | 324.1 |
| PURITY: | 97% (HPLC) |
| APPEARANCE: | Yellow oil. |
| CAS: | 82005-12-7 |
| SOURCE/HOST: | Isolated from sponge *Axinella carteri*. |
| SOLUBILITY: | Soluble in DMSO (5 mg/ml). |
| SHIPPING: | AMBIENT |
| STORAGE: | −20° C. |
| HAZARD: | TOXIC. |
| HANDLING: | Protect from light. |

-continued

| Oroidin | |
|---|---|
| FORMULA: | $C_{11}H_{11}Br_2N_5O$ |
| MW: | 389.1 |
| CAS NUMBER: | 34649-22-4 |
| SOURCE/HOST: | Isolated from *Stylissa* sp. |
| PURITY: | 97% (HPLC, NMR) |
| IDENTITY: | Identity determined by $^1$H-NMR, $^{13}$C-NMR and MS. |
| APPEARANCE: | Amorphous solid. (Actual lot: beige solid) |
| SOLUBILITY: | Soluble in 100% ethanol or DMSO. |
| SHIPPING: | AMBIENT |
| STORAGE: | −20° C. |
| HANDLING: | Protect from light. Keep cool and dry. |

The compounds were ordered and screened on the EASY-HIT assay and the HIV-1 RT biochemical assay at molarities below 100 μM in order to assess their ability inhibit HIV-1 replication. Statistical significances were determined using one-way ANOVA.

2.2. Human Immunodeficiency Virus, full Virus Screening (EASY-HIT)

The EASY-HIT assay (Kremb et al. [11]) is based on HIV-1 susceptible reporter cells (LC5-RIC) that contain a stably integrated fluorescent reporter gene that is activated upon successful HIV-1 infection and expression of the early viral proteins Rev and Tat. LC5-RIC were seeded into 96-well plates (μCLEAR-Plate Black; Greiner Bio-One, Kremsmuenster, Germany) using only the 60 inner wells to avoid variations in the culture conditions in the outer wells. Cells were seeded at a density of 10,000 cells per well 24 hours prior to infection. SPE fractions for the biological replicates C26, C14 and D5, were tested in a serial 1:2-dilution with a maximum of 3% methanol or approximately 75 μg/ml for the *S. carteri* fraction 1 mixture on the EASY-HIT assay [11]. For the HPLC fractions, SPE fraction 1 HPLC fractions 1-11, were tested on the EASY-HIT assay for biological replicates C26, C14 and D5. The authentic samples of HD, DBH, and oroidin were screened at 3.1 μM, 6.25 μM, 12.5 μM, 25 μM, and 50 μM. All samples were tested in triplicates. After compound addition, LC5-RIC cells were infected by adding 20 μl of HIV-1 inoculum (approx. 28.8 ng of p24 for HIV-1LAI derived from HEK 293T cells) to each well of the plate. Cells were incubated at standard cell culture conditions for 48 hours after infection and were subsequently assayed for reporter expression and cell viability.

Reporter expression was determined by measuring the total fluorescent signal intensity of each culture with a fluorescence microplate reader (Fluoroskan Ascent; ThermoFisher, Schwerte, Germany) at an excitation filter wavelength of 544 nm and an emission filter wavelength of 590 nm or with a Tecan infinite M200 (Tecan, Crailsheim, Germany) at the monochromator wavelengths 552 nm for excitation and 596 for emission. Statistical significances were determined using one-way ANOVA.

2.2.1. MTT Cell Proliferation Assay

The colorimetric assay MTT was used in order to assess the viability and activity of LC5-RIC cells exposed to the unknown sponge mixtures, SPE fraction 1 and HPLC fractions 1-11, for three biological replicates. This cell vitality assay provides a visualization of the process where mitochondrial enzymes reduce the yellow MTT to purple formazan (ATCC, MTT cell proliferation assay). After reading the HIV reporter expression, cultures were incubated with 100 μl of MTT solution (0.5 mg of MU; Sigma, Taufkirchen, Germany) in 100 μl of culture medium for 2 hours. MTT solution was removed and 100 μl of lysis solution (10% [wt/vol] SDS and 0.6% [vol/vol] acetic acid in dimethyl sulfoxide [DMSO]) was added. The formazan concentrations of the test compounds and the uninfected control cultures were determined by an ELISA plate reader (Tecan Infinite M200, Tecan Germany GmbH, Crailsheim) and scanned with a test wavelength of 570 nm and a reference wavelength of 630 nm. Statistical significances were determined using one-way ANOVA.

2.3 Human Immunodeficiency Virus, Reverse Transcriptase Biochemical Test

The HIV-1 reverse transcriptase inhibition assay was carried out using the commercial kit EnzChek® Reverse Transcriptase Assay (Invitrogen, San Jose, Calif., USA). The reverse transcriptase is a heterodimer with the p66 and the p51 subunits with RNase H activity located in the last 15 KDa of the p66 HIV Reverse transcriptase (Calbiochem, Merck-Millipore). Polymerase activity was assessed by its ability to produce RNA-DNA heteroduplexes from a mixture of a long poly (A) template, an oligo dT primer and dTTP which is then detected by PicoGreen® dsDNA quantitation reagent. The single compound and controls were performed in triplicated in a 384-well plate format, each with a total reaction mixture of 50 μL. To begin, the poly (A) template was annealed to the oligo dT primer for one hour, then diluted 200 fold in polymerization buffer. Reverse transcriptase (1.2 μl) was added per 300 reactions. This mixture was kept on ice and aliquoted to each well with test compounds. The reaction was incubated at room temperature for one hour and then 2 μl of 50 nM EDTA was added to stop the reaction. The RNA-DNA heteroduplex was labeled with PicoGreen and incubated for 5 minutes and then detected with the use of a SpectraMax® Paradigm® Multi-mode Microplate Detection Platform (Molecular Devices, Sunnyvale, Calif., USA) by scanning at 480 nm excitation wavelength and 520 nm emission wavelength. The authentic standards of HD, DBH, and oroidin were screened at 3.1 μM, 6.25 μM, 12.5 μM, 25 μM, 50 μM, and 100 μM. Statistical significances were determined using a one-way ANOVA.

REFERENCES AND NOTES

No admission is made that any reference cited herein and/or cited below as endnotes 1-23 is prior art.

1. (UNAIDS). Global report: Unaids report on the global aids epidemics 2013. *JUNPoHA* 2013, UNAIDS/JC2502/1/E.
2. Downs, C. A. et al., Oxidative stress and seasonal coral bleaching. *Free Radical Biology & Medicine* 2002, 33, 533-543.
3. Martinez, J. P. et al., A. Antiviral drug discovery: Broad-spectrum drugs from nature. *Nat Prod Rep* 2015, 32, 29-48.
4. Clercq, D. Curious discoveries in antiviral drug development: The role of serendipity. *Medicinal Research Reviews* 2015, 00, No. 0, 1-22, 2015.
5. Newman, D. J. et al., Therapeutic agents from the sea: Biodiversity, chemo-evolutionary insight and advances to the end of Darwin's 200th year. *Diving and Hyperbaric Medicine* 2009, 39, 216-225.
6. Butler, M. S., et al., Natural product and natural product derived drugs in clinical trials. *Natural Product Reports* 2014, 31, 1612-1661.
7. Hu, Y. W., et al., Statistical research on the bioactivity of new marine natural products discovered during the 28 years from 1985 to 2012. *Mar Drugs* 2015, 13, 202-221.
8. Yarnold, J. E., et al., High resolution spatial mapping of brominated pyrrole-2-aminoimidazole alkaloids distributions in the marine sponge *Stylissa flabellata* via maldi-mass spectrometry imaging. *Mol Biosyst* 2012, 401 8, 2249-2259.
9. Keifer, P. A., et al., Bioactive bromopyrrole metabolites from the caribbean sponge agelas-conifera. *J Org Chem* 1991, 56, 2965-2975.
10. Breton, J. J., et al., The natural product hymenialdisine inhibits interleukin-8 production in U937 cells by inhibition of nuclear factor-kappa B. *J Pharmacol Exp Ther* 1997, 282, 459-466.
11. Kremb, S., et al., Easy-hit: HIV full-replication technology for broad discovery of multiple classes of HIV inhibitors. *Antimicrobial Agents and Chemotherapy* 2010, 54, 5257-5268.
12. Kremb, S., et al., Aqueous extracts of the marine brown alga lobophora variegata inhibit hiv-1 infection at the level of virus entry into cells. *PloS one* 2014, 9, e103895.
13. Helfer, M., et al., The root extract of the medicinal plant pelargonium sidoides is a potent hiv-1 attachment inhibitor. *PloS one* 2014, 9, e87487.
14. Forenza, S., et al., New bromo-pyrrole derivatives from sponge agelas-oroides. *J Chem Soc Chem Comm* 1971, 1129-&.
15. Sharma, G. M. et al, Characterization of a yellow compound isolated from the marine sponge phakellia-flabellata. *Journal of the Chemical Society-Chemical Communications* 1980, 435-436.
16. Cimino, G. et al. Isolation and x-ray crystal-structure of a novel bromo-compound from 2 marine sponges. *Tetrahedron Lett* 1982, 23, 767-768.
17. Mohammed, R., et al., Cyclic heptapeptides from the jamaican sponge *Stylissa* caribica. *J Nat Prod* 2006, 69, 1739-1744.
18. Al-Mourabit, A., et al. Biosynthesis, asymmetric synthesis, and pharmacology, including cellular targets, of the pyrrole-2-aminoimidazole marine alkaloids. *Nat Prod Rep* 2011, 28, 1229-1260.
19. Meijer, L. et al, Inhibition of cyclin-dependent kinases, gsk-3 beta and ck1 by hymenialdisine, a marine sponge constituent. *Chem Biol* 2000, 7, 51-63.
20. Debebe, Z. et al., Iron chelators of the di-2-pyridylketone thiosemicarbazone and 2-benzoylpyridine thiosemicarbazone series inhibit hiv-1 transcription: Identification of novel cellular targets-iron, cyclin-dependent kinase (cdk) 2, and cdk9 (vol 79, pg 185, 2011). *Mol Pharmacol* 2011, 80, 1190-1190.
21. Curman, D. et al. Inhibition of the g2 DNA damage checkpoint and of protein kinases chk1 and chk2 by the marine sponge alkaloid debromohymenialdisine. *J Biol Chem* 2001, 276, 17914-17919.
22. Goh, W. C., et al. HIV-1 vpr increases viral expression by manipulation of the cell cycle: A mechanism for selection of vpr in vivo. *Nat Med* 1998, 4, 65-71.
23. Bugni, T. S. et al., Marine natural product libraries for high-throughput screening and rapid drug discovery. *J Nat Prod* 2008, 71, 1095-1098.

TABLE 1

HPLC gradient used to separate the *S. carteri* SPE fraction 1 into HPLC fractions 1-11.

| Time | % H$_2$0 | % Acetonitrile |
| --- | --- | --- |
| 0 min | 65 | 35 |
| 1 min | 65 | 35 |

TABLE 1-continued

HPLC gradient used to separate the *S. carteri* SPE fraction 1 into HPLC fractions 1-11.

| Time | % H$_2$0 | % Acetonitrile |
| --- | --- | --- |
| 20 min | 30 | 70 |
| 26 min | 30 | 70 |
| 28 min | 65 | 35 |
| 30 min | 65 | 35 |

TABLE 2

LC-MS gradient used to characterize the bioactive compounds of *S. carteri* SPE fraction 1, HPLC fraction 2 and 6.

| Time | % H$_2$0 | % MeOH | Formic acid in each solvent |
| --- | --- | --- | --- |
| 0 min | 90 | 10 | 0.10% |
| 5 min | 90 | 10 | 0.10% |
| 40 min | 10 | 90 | 0.10% |
| 50 min | 10 | 90 | 0.10% |
| 55 min | 90 | 10 | 0.10% |
| 60 min | 90 | 10 | 0.10% |

What is claimed is:

1. A method comprising:
   (i) subjecting crude extracts of *Stylissa carteri* sponge to solid phase extraction to produce a library of fractions;
   (ii) conducting at least one first screening assay of the library of fractions for inhibition of HIV and for cytotoxicity, including selecting at least one fraction for further fractionation;
   (iii) fractionating the at least one fraction further to produce at least one additional fraction;
   (iv) conducting at least one second screening assay of the at least one additional fraction for inhibition of HIV and for cytotoxicity, including selecting one or more fractions with decreased cytotoxicity for further identification study; and
   (v) identifying HIV inhibiting molecule candidate(s) based on the inhibition of HIV and decreased cytotoxicity.

2. The method of claim 1, wherein the library of fractions comprises at least four fractions.

3. The method of claim 1, wherein the first screening assay is an HIV replication assay.

4. The method of claim 1, wherein the second screening assay is an HIV replication assay.

5. The method of claim 1, wherein the fractionating is an HPLC fractionating.

6. The method of claim 1, wherein the identifying molecule comprises use of LC-MS.

7. The method of claim 1, wherein the identifying molecule comprises determining which molecules appear in multiple fractions.

8. The method of claim 1, wherein the identified molecules are further tested with a biochemical assay.

9. The method of claim 1, wherein the identified molecule is a pyrrole-imidazole alkaloid compound.

10. The method of claim 1, wherein the identified molecule is a brominated pyrrole-2-aminoimidazole alkaloid compound.

11. The method of claim 1, wherein the identified molecule is oroidin.

* * * * *